United States Patent [19]

Kolobov et al.

[11] Patent Number: 5,916,878
[45] Date of Patent: Jun. 29, 1999

[54] γ-GLUTAMYL AND β-ASPARTYL CONTAINING IMMUNOMODULATOR COMPOUNDS AND METHODS THEREWITH

[75] Inventors: Alexander A. Kolobov, Sestroetsk; Andrey S. Simbirtsev, St. Petersburg, both of Russian Federation

[73] Assignee: Edward T. Wei, Berkeley, Calif.

[21] Appl. No.: 09/031,842

[22] Filed: Feb. 27, 1998

Related U.S. Application Data

[63] Continuation-in-part of application No. 08/634,718, Apr. 18, 1996, Pat. No. 5,744,452.

[30] Foreign Application Priority Data

| Nov. 28, 1995 | [RU] | Russian Federation | 95119704 |
| Nov. 28, 1995 | [RU] | Russian Federation | 95120266 |
| Dec. 25, 1997 | [RU] | Russian Federation | 97120940 |

[51] Int. Cl.$^6$ .......................... A61K 38/00; A61K 31/40; A61K 31/38; C07D 333/22
[52] U.S. Cl. ........................ 514/19; 514/419; 514/438; 548/496; 549/76
[58] Field of Search ........................... 514/19, 419, 438; 548/496; 549/76

[56] References Cited

U.S. PATENT DOCUMENTS

| 4,125,626 | 11/1978 | Orlowski et al. . | |
| 4,568,489 | 2/1986 | Floyd . | |
| 4,758,551 | 7/1988 | Meister et al. . | |
| 5,206,220 | 4/1993 | Hilton . | |
| 5,736,519 | 4/1998 | Deigin et al. ............... | 514/18 |
| 5,744,452 | 4/1998 | Kolobov et al. ............ | 514/19 |

FOREIGN PATENT DOCUMENTS

| 92/17191 | of 1992 | WIPO . |
| 93/08815 | of 1993 | WIPO . |
| 96/40740 | of 1996 | WIPO . |

OTHER PUBLICATIONS

Christian, J.S., "A Review of the Pharmacology, Clinical Applications, and Toxicology of Thymopentin," *Transgenica: The Journal of Clinical Biotechnology*, 1, pp. 23–34 (1994).

Prezioso et al., "γ–Glutamyltraspeptidase Expression Regulates the Growth–Inhibitory Activity of the Anti–Tumor Prodrug γ–L–glutaminyl–4–hydroxy–3–iodobenzene," *Int. J. Cancer*, 56, pp. 874–879 (1994).

Li Kam Wa et al., "The Antiatriuretic Action of γ–L–glutamyl–5–hydroxy–L–tryptophan is Dependent on its Decarboxylation to 5–hydroxytryptamine in Normal Man," *Br. J. Clin. Pharmac.*, 387, pp. 265–269 (1994).

Illum, Lisbeth, "The Nasal Delivery of Peptides and Proteins," *Trends in Biotechnology*, 9, pp. 284–289 (1991).

Goldstein et al., "Thymopoietin to Thymopentin: Experimental Studies," *Thymopentin in Experimental and Clinical Medicine, Survey of Immunologic Research*, 4, Supp. 1, pp. 1–10 (1985).

Gillis et al., "T–Cell Growth Factor: Parameters of Production and Quantitative Assay for Activity," *J. Immunol.*, 120:6, pp. 2027–2032 (1978).

Wellner, Daniel, "Separation of γ–Glutamyl Amino Acids by Ion–Exchange Chromatography," *Methods in Enzymology*, 113, pp. 564–566, 1985.

Hirata et al., "Studies on Separation of Amino Acids and Related Compounds. VIII. Separation of L–Aspartyl–(α, β)–L–histidine and of L–Glutamyl–(α,γ)–L–Histidine," *Bulletin of the Chemical Society of Japan*, 45, pp. 1790–1794, 1972.

Hasegawa et al., "γ–Glutamylpeptide Formative Activity of *Corynebacterium glutamicum* by the Reverse Reaction of the γ–Glutamylpeptide Hydrolytic Enzyme," *Agric. Biol. Chem.*, 42:2, pp. 371–381, 1978.

Greene and Wuts, "Carbamates" in chapter entitled "Protection for Imidazoles, Pyrroles, and Indoles" from *Protective Groups in Organic Synthesis*, New York: John Wiley & Sons, Inc., p. 387, 1991.

*Primary Examiner*—Deborah C. Lambkin
*Attorney, Agent, or Firm*—Majestic, Parsons, Siebert & Hsue

[57] ABSTRACT

Synthetic immunomodulatory molecules having a γ-L-glutamyl-, a γ-D-glutamyl, a β-L-aspartyl, or a β-D-aspartyl moiety at the amino terminus are provided as illustrated by Formula A.

$$\text{R—NH—CH}\!\!\left(\!\!\begin{array}{c}\text{CH}_2\!\!\end{array}\!\!\right)_{\!\!n}\!\!\text{C—X}$$
$$\underset{\text{COOH}}{|}\quad\underset{\text{O}}{\|}$$

In Formula A, "n" is 1 or 2, R is hydrogen, acyl or alkyl, and X is an aromatic or heterocyclic amino acid or its derivative. A particularly preferred embodiment is γ-D-glutamyl-L-tryptophan, which has immunomodulatory activity.

14 Claims, No Drawings

γ-GLUTAMYL AND β-ASPARTYL CONTAINING IMMUNOMODULATOR COMPOUNDS AND METHODS THEREWITH

RELATED APPLICATION

This is a continuation-in-part of application Ser. No. 08/634,718, filed Apr. 18, 1996, U.S. Pat. No. 5,744,452.

FIELD OF THE INVENTION

The invention generally relates to immunostimulant compounds, and more particularly relates to immunostimulant compounds including either a γ-L-glutamyl, a γ-D-glutamyl, a β-L-aspartyl, or β-D-aspartyl moiety that stimulates maturation and differentiation of certain classes of white blood cells within the body. This selective stimulation of white blood cell differentiation and proliferation enhances the body's defenses against disease-causing organisms and also modulates and ameliorates self-inflammatory conditions.

BACKGROUND OF THE INVENTION

The immune system is a network of cells adapted to protect the organism against pathogens and cells that are not recognized as "self." Once the immune system is activated, it enlists the participation of a variety of cells and molecules to mount an effector function designed to eliminate the "non-self" entity within the body. Lymphocytes are cells of the immune system that are capable of specifically recognizing and selectively eliminating foreign entities. By contrast to other cells of the immune system, such as neutrophils which are considered non-specific in their reactions to invaders, the characteristics of lymphocytes confer specificity, diversity, memory and self/nonself recognition to the immune response.

There are two major populations of lymphocytes: B lymphocytes and T lymphocytes. B lymphocytes originate and mature within the bone marrow and are responsible for formation of antibody molecules. T lymphocytes also arise from the bone marrow but mature in the thymus. There are two major subpopulations of T-cells: T helper cells and T cytotoxic cells. The two types of T cells can be distinguished by the presence of one of two membrane glycoproteins, either CD4 or CD8. The T-helper cells (which express CD4) when activated by antigen-complexes (foreign molecules coupled to special proteins) respond by secreting various growth factors known collectively as cytokines. These cytokines are signals that activate other cells of the immune system, including the T-cytotoxic cells. The T-cytotoxic cells (which express CD8) when activated, proliferate and differentiate into cytotoxic T lymphocytes (CTL) which are able to monitor for and eliminate from the body pathogenic cells, foreign cells, virus-infected cells, and tumor cells.

The normal development, maturation and differentiation of T lymphocytes are regulated by peptide hormones secreted by thymic cells. One such hormone is the 49-amino acid residue peptide, thymopoietin. Residues 32–36 of thymopoietin, Arg-Lys-Asp-Val-Tyr, retain the biological activities of thymopoietin, and are the basis for an immunomodulatory drug called thymopentin. The therapeutic applications of thymopentin include use for rheumatoid arthritis, dermatologic conditions, infections by bacteria, virus and fungi, reversal of immune depression due to surgery or to cancer therapy, potentiation of responses to hepatitis B virus vaccination, and treatment of acquired immunodeficiency syndrome (AIDS), a condition in which T-helper (CD4) cells are specifically attacked by the virus (Christian, J. S., "A Review of the Pharmacology, Clinical Applications, and Toxicology of Thymopentin," *Transgenica: The Journal of Clinical Biotechnology,* 1, pp. 23–34, 1994).

A second compound with similar properties to thymopentin is the dipeptide, Glu-Trp, called thymogen. The sequence -Glu-Trp- also occurs in the molecule that is precursor for the synthesis of thymopoietin but -Glu-Trp- is not part of the 49-amino acid hormone nor is this dipeptide recognized as being a contributor to biological activity of thymopoietins. Thymogen was discovered and was used primarily in Russia for the prophylaxis and treatment of infections. Thymogen was used for the enhancement of immune function after damage of lymphocytes by accidental exposure to irradiation as a result of the Chernobyl incident. (Khavinson et al., WO 92/17191 and WO 93/08815, "Pharmaceutical Dipeptide Compositions and Methods of Use Thereof").

γ-L-Glutamyl derived peptides occur naturally in the body, the most well-known example being the tripeptide glutathione. Synthetic γ-L-glutamyl-molecules have also been used as candidate drugs. These candidates are called "prodrugs" because the γ-L-glutamyl moiety is used as a carrier for the active portion of the molecule. For example, γ-L-glutaminyl-4-hydroxy-3-iodobenzene demonstrates anti-tumor activity in human and in mouse melanoma cell lines. It is thought that the anti-tumor activities of this compound is due to enzymatic release of 4-hydroxy-3-iodobenzene near the tumor cells (Prezioso et al., "γ-Glutamyltranspeptidase Expression Regulates the Growth Inhibitory Activity of the Anti-tumor Prodrug γ-glutaminyl-4-hydroxy-3-iodobenzene," *International Journal of Cancer,* 56, pp. 874–879, 1994). Also, γ-L-glutamyl-dopamine and γ-L-glutamyl-5-hydroxy-tryptophan have been described as prodrugs that might carry and supply dopamine and 5-hydroxy-tryptophan to brain neurons (Likamwa et al., "The Antinatriuretic Action of γ-L-glutamyl-5-hydroxy-L-tryptophan is Dependent on its Decarboxylation to 5-hydroxytroptamine in Normal Brain," *British Journal of Clinical Pharmacology,* 387:265–269, 1994).

PCT document WO 96/40740, published Dec. 19, 1996, inventors Deigin and Korotkov disclose peptides of formula X-A-D-Trp-Y (I), where: A=D-Glu or D-isoglutamic acid (D-iGlu); X=H, Gly, Ala, Leu, Ile, Val, Nva, Pro, Tyr, Phe, Trp, D-Ala, D-Leu, D-Ile, D-Val, D-Nva, D-Pro, D-Tyr, D-Phe, D-Trp, γ-aminobutyric acid or ε-aminocaproic acid; Y=Gly, Ala, Leu, Ile, Val, Nva, Pro, Try, Phe, Trp, D-Ala, D-Leu, D-Ile, D-Val, D-Nva, D-Pro, D-Try, D-Phe, D-Trp, γ-aminobutyric acid, ε-aminocaproic acid, OH, or 1–3C substituted amino. Compounds (I) are said to have immunosuppressant activity (e.g. inhibiting proliferation of spleen cells) and to be useful in human and veterinary medicine and experimental biochemistry.

SUMMARY OF THE INVENTION

"Bestim," an acronym of the coined phrase "best immunomodulator," is the name given to an embodiment of a new class of compounds to which this invention pertains and which have immunomodulatory properties. The parent patent application Ser. No. 08/634,718, of which this is a continuation-in-part, describes and claims several compounds in the new class of compounds, and claims an immunomodulatory therapeutic method through use of these compounds. The Bestim compound itself has the chemical structure of γ-L-glutamyl-L-tryptophan.

The new class of synthetic immunomodulatory molecules are illustrated by Formula 1.

FORMULA 1

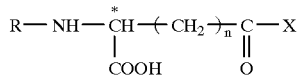

In Formula 1, R is hydrogen, acyl, alkyl, or a peptide fragment, X is an aromatic or heterocyclic amino acid or its derivative, and n is 1 or 2. We have discovered that included as members of the new class (in addition to Bestim, γ-L-glutamyl-L-tryptophan) are those compounds where R=hydrogen and X=L-tryptophan and D-tryptophan, such as γ-D-glutamyl-L-tryptophan, γ-L-glutamyl-D-tryptophan, β-L-aspartyl-L-tryptophan, and β-D-aspartyl-L-tryptophan. The α carbon marked with an asterisk in Formula 1 has a stereoconfiguration, when n is 2, that is different from the stereoconfiguration of X. A particularly preferred embodiment is γ-D-glutamyl-L-tryptophan. The peptides of Formula 1 can form pharmaceutically acceptable salts with any non-toxic, organic, or inorganic acid. Salts of the carboxylic groups include the non-toxic carboxylic acid salts formed with any suitable inorganic or organic bases.

The embodiment Bestim has a potent immunostimulatory activity when tested in various experimental assay systems in vitro and in vivo. The mechanism of its biological action is related to the induction of differentiation of bone marrow T-lymphocyte precursors, stimulation of lymphocyte proliferation, and increase in production of various cytokines, including interleukin-2. The net result of Bestim's pharmacological effect is a selective increase in the number of T-helper lymphocytes, that is, cells that contain the CD4 marker.

Preclinical studies of Bestim demonstrate immunostimulatory activity at sub-nanomolar concentrations. In vivo it acts at doses of 10 ng to 1 μg per kg body weight and has no observable toxicity at doses 500 to over a million-fold higher than the immunostimulatory dose. In animal studies, it is active after oral administration.

In preliminary studies in humans, Bestim increased immune function as measured by laboratory changes of lymphocyte function. These laboratory changes were accompanied by positive indicators of benefit in clinical outcome.

One of the new analogs, γ-D-glutamyl-L-tryptophan, has been found to have an even higher biological activity compared to that of Bestim and with IL-2 induction observed in a more wide dose range.

A drug designated as an "immunodulatory drug" has a well-defined set of actions. Bestim and its analogs are effective as a drug for immunotherapy of infectious diseases and for reinstatement of immune reactivity previously decreased by exposure to radiation or other stress factors such as cancer chemotherapy or surgery.

Thus, the Formula 1 compounds possessing immunomodulatory activity are usefully administered to patients to modify immunodeficiency caused by natural or drug-induced states, administered to patients to ameliorate and to reduce the risks infections from micro-organisms, especially administered to hospitalized patients, to burn victims, to patients undergoing surgery, to patients undergoing cancer chemotherapy, because such individuals are especially prone to infections. Further, the Formula 1 immunomodulatory compounds may be administered to patients with symptomatic or asymptomatic viral infections, in order to facilitate viral elimination and to enhance immune surveillance of pathogenic organisms and thus to reduce the likelihood of recurrence of disease, for example, for individuals who are sick from or are carriers of herpes viruses, varicella viruses, hepatitis viruses and HIV, administered to patients with diseases that alter natural cells so that they are recognized as "foreign" by the body, for example, in conditions such as cancer, and administered to patients with self-inflammatory (autoimmune) diseases such as rheumatoid arthritis, multiple sclerosis, scleroderma—in order to adjust the immune system to equilibrium.

In addition to these uses with patients at high risk of disease or expressing symptoms of disease, the Formula 1 immunomodulatory compounds may be administered to healthy populations in anticipation of epidemic infections, for example, in conjunction with influenza vaccinations, or to invigorate the immune response to pathogens in conjunction with vaccinations, for example, for vaccination against hepatitis - - - the technical term for this is the use of the invention as an "adjuvant" to vaccination.

These uses may be administered by dosages in the range of about 1 ng to about 1000 μg per kg of body weight, given as a single dose or intermittently over a period of up to a month or more, and the routes of delivery are preferably by parenteral injection, by oral or nasal inhalation, or by oral ingestion.

DETAILED DESCRIPTION OF THE PREFERRED EMBODIMENTS

Broadly, compounds of this invention are unique chemical substances that modulate the population of T-helper cells to optimum levels in the host. For example, modulation of the immune system to increase the number of T-helper cells increases the organism's ability to cope with infections from bacteria or viruses. Modulation to increase the number of T-helper cells also helps the body to fight against cancer cells that have become foreign to the host. Alternatively, these substances also enable the host to adjust to diseases arising from disarrangement of self-recognition processes in which there is excessive attack by host T-cells against endogenous tissues. In such instances, the inventive compounds modulate the T-cell population so that the signs and symptoms of self-directed inflammatory (autoimmune) diseases such rheumatoid arthritis and multiple sclerosis are ameliorated.

"Bestim," an acronym of the coined phrase "best immunomodulator," is the name given to one embodiment of a new class of compounds to which this invention pertains and which have immunomodulatory properties. It has no observable toxicity at doses 500 to over 500,000 times higher than immunostimulatory dose. The Bestim compound itself has the chemical structure of γ-L-glutamyl-L-tryptophan. The new class of synthetic immunomodulatory molecules have a γ-L-glutamyl- moiety, a γ-D-glutamyl-moiety, a β-L-aspartyl moiety, or a β-D-aspartyl moiety at the amino terminus, as illustrated by Formula 1.

FORMULA 1

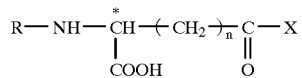

In Formula 1, n is 1 or 2, R is hydrogen, acyl or alkyl, and X is an aromatic or heterocyclic amino acid or its derivative, preferably where X=L-tryptophan and D-tryptophan.

Appropriate derivatives of the aromatic or heterocyclic amino acids for "X" are: amides, mono- or di-($C_1$-$C_6$) alkyl substituted amides, arylamides, and ($C_1$-$C_6$) alkyl or aryl esters. Appropriate acyl or alkyl moieties for "R" are: branched or unbranched alkyl groups of 1 to 6 carbons, acyl groups from 2 to 10 carbon atoms, and blocking groups such as carbobenzyloxy and t-butyloxycarbonyl. The α carbon marked with an asterisk in Formula 1 has a stereoconfiguration, when n is 2, that is different from the stereoconfiguration of X.

Included as members of the new class (in addition to Bestim, γ-L-glutamyl-L-tryptophan) are compounds such as γ-L-glutamyl-$N_{in}$-formyl-L-tryptophan, N-methyl-γ-L-glutamyl-L-tryptophan, N-acetyl-γ-L-glutamyl-L-tryptophan, γ-D-glutamyl-L-tryptophan, γ-L-glutamyl-D-tryptophan, β-L-aspartyl-L-tryptophan, and β-D-aspartyl-L-tryptophan.

The peptides of Formula 1 can form pharmaceutically acceptable salts with any non-toxic, organic or inorganic acid. Illustrative organic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, benzoic, hydroxygenzoic, phenylacetic, cinnamic, salicylic, 2-phenoxybenzoic and sulfonic acids as methane sulfonic acid and 2-hydroxyethane sulfonic acid. Salts of the carboxylic groups include the non-toxic carboxylic acid salts formed with any suitable inorganic or organic bases. Illustratively, these salts include those of alkali metals, as for example, sodium and potassium, alkaline earth metals, such as calcium and magnesium, light metals of Group IIIA including aluminum and organic primary, secondary, and tertiary amines, as for example trialkyl-amines, including triethylamine, procaine, dibenylamine, 1-ethenamine, N,N-dibenzyl-ethylenediamine, dihydroabiethylamine, (N-(lower)alkyl-piperidine, and any suitable amine.

The presence of the γ-L-glutamyl or β-aspartyl moiety in the Formula 1 inventive compounds had been believed to confer two important properties: resistance to degradation by aminopeptidases and increased potency. However, one of the inventive analogs, γ-D-glutamyl-L-tryptophan, has been found to have an even higher biological activity than Bestin and a wider dose range. This particularly preferred embodiment of the invention is sometimes referred to as "SCV-07."

Toxicity

Acute and sub-acute toxicity studies were conducted in animals with Bestim according to conditions of good-laboratory practices. Bestim, prepared as a sterile lyophilized powder in ampoules, was dissolved in sterile 0.9% NaCl solution and injected intramuscularly in all experiments.

Acute toxicity: Rodents (mice and rats) and dogs were randomized into groups of equal numbers of males and females. Animals were inspected daily for 14 days after a single dose of Bestim (intramuscular):

mice—5000.0 mg/kg
rats—500.0 mg/kg
dogs—500.0 mg/kg

Body weight, overall appearance and behavior were evaluated each day and, at the end of two weeks, macroscopic and histopathological examinations of the internal organs (heart, lungs, pleural and peritoneal cavities, muscles, stomach, small and large intestine, liver, spleen, pancreas, kidneys, bladder, thyroid, brain, skin and testes/ovaries) of all animals were conducted.

No deaths were observed in any of the animals tested and the recorded parameters of general appearance, behavior, body weight, hematological, biochemical and physiological indices, and macroscopic and histopathological examination of internal organs were all within normal limits.

Subacute Toxicity Studies: In a second set of experiments, Bestim was administered for longer durations, accordingly:

rats: 1 mg/kg and 100 mg/kg, administered intramuscularly daily for 3 months and for 6 months dogs: 1 mg/kg, 10 mg/kg and 100 mg/kg, administered intramuscularly daily for 1 month and for 3 months.

Repeated injection of Bestim in rats did not cause death in any animal, or produce changes in behavior, or in hematological, biochemical, or physiological parameters. The morphological appearance of all organs at the macroscopic and histological levels were normal. Both doses in rats induced a slight increase in body weight in experimental animals.

Repeated injection of Bestim in dogs did not cause death in any animal, or produce changes in behavior, body weight, hematological, biochemical or physiological parameters. Macroscopic and histological examination of all examined organs showed no significant changes. There were no local inflammatory reactions at the site of injection.

In conclusion, these toxicity tests showed that Bestim is free of acute or subacute toxic properties in rodents and dogs. The tested doses relative to the expected doses for therapeutic trials were on the order of 5,000,000-fold for single administration and 100-fold for repeated administration.

The toxicity of four peptides (three of which were inventive) in vitro was also assessed using murine thymocytes. Thymocytes were washed twice, resuspended in RPMI 1640 medium, containing 2% fetal calf serum. Cell suspension was placed into 96-well plate ($1 \times 10^6$ cells per well). Then the peptides (or carrier for control wells) were added into wells at desirable concentrations. Cells were incubated with peptides or carrier during 4 hours at 37° C. in $CO_2$ incubator. After the incubation the cell viability was calculated microscopically using Eosin B staining. The results are shown in Table A.

TABLE A

| Peptide Doses (μg/ml) | Cell viability % |
|---|---|
| Comparative γ-D-Glu-D-Trp | |
| 100 | 94.7 ± 0.3* |
| 10 | 97.3 ± 0.33 |
| 1 | 96.7 ± 0.88 |
| 0.1 | 98.3 ± 0.3 |
| 0.01 | 97.5 ± 0.5 |
| Inventive γ-D-Glu-L-Trp | |
| 100 | 95.3 ± 0.88 |
| 10 | 96.7 ± 1.86 |
| 1 | 97.3 ± 1.2 |
| 0.1 | 96.7 ± 0.88 |
| 0.01 | 96.3 ± 0.67 |
| Inventive γ-L-Glu-D-Trp | |
| 100 | 95.0 ± 1.15 |
| 10 | 95.3 ± 1.45 |
| 1 | 95.3 ± 0.67 |

TABLE A-continued

| Peptide Doses (μg/ml) | Cell viability % |
|---|---|
| 0.1 | 97.0 ± 0.58 |
| 0.01 | 96.0 ± 0.58 |
| Inventive γ-L-Glu-L-Trp | |
| 100 | 96.7 ± 2.85 |
| 10 | 96.0 ± 0.58 |
| 1 | 97.7 ± 1.2 |
| 0.1 | 98.0 ± 1.0 |
| 0.01 | 96.0 ± 0.58 |
| Control | 97.0 ± 0.58 |

*the difference is statistically significant in comparison with control, $p < 0.05$ However, the comparative peptide, γ-D-glutamyl-D-tryptophan, was found to reduce cell viability (Table A) and thus to be cytotoxic at a dose of 0.1 mg/ml.

Goldstein and Audhya ("Thymopoietin to Thymopentin: Experimental Studies" in Thymopentin in Experimental and Clinical Medicine, Surv. Immunol. Res., 4, pp. 1–10, 1985) introduced the concept that immunomodulatory drugs act to restore immune imbalances, whether the imbalances are in the hyporesponsive or hyperresponsive state. The bi-directional activity of these drugs occur because of the nature of bioregulation in which imbalances are restored to an equilibrium set-point. In the case of hyporesponsiveness, administration of hormones that regulate T-lymphocytes acts to optimize and up-regulate the function of the self-defense system so that non-self organisms are more easily rejected. In the case of hyperresponsiveness, the administration of immunomodulatory drugs appears to dampen autoimmune processes in which the mistaken attack of useful "self" entities is now diminished. The categories of clinical applications of Bestim in hyporesponsive and hyperresponsive immune states are discussed and examples delineated.

Hyporesponsiveness or Immunodeficient Conditions

Immunodeficiency states fall into three general etiologic categories. First, there is immunosuppression that occurs as a consequence of disease processes. Second, there are immunodeficiencies that arise because of therapy for other diseases, so-called iatrogenic immunodeficiencies. Third, immunodeficiencies may result from direct attack of T-lymphocytes by the human immunodeficiency virus (HIV) that causes the acquired immunodeficiency syndrome (AIDS).

Common disease processes that lead to immunodeficiency are malnutrition, neoplasias, aging, and infections. Malnourished people, patients with advanced widespread cancers and people with debilitating illnesses become sick and die more often because impaired cell-mediated and humoral immune responses increase susceptibility to infections by a variety of organisms. A state of generalized deficiency in immune responses is called anergy. Various types of infections, especially viral infections, lead to immunosuppression. A drug such as Bestim, capable of making the T-helper lymphocyte components of the immune system more robust, will be an important therapeutic agent for increasing the resistance of the patient to infections. For example, Bestim or its analogs, may be:

administered to patients, especially older patients, before or just after admissions to hospitals in order to reduce the risks of nosocomial (hospital-induced) infections, a common and severe clinical problem administered to burn victims, because such individuals are especially prone to infections administered to patients in anticipation of epidemic infections, for example, in conjunction with influenza vaccinations or hepatitis vaccinations, to invigorate the immune response to pathogens administered to patients with asymptomatic viral infections, in order to enhance immune surveillance of pathogenic organisms and reduce the likelihood of recurrence of disease, for example, for individuals who are carriers of herpes viruses, varicella viruses, hepatitis viruses and HIV.

Iatrogenic immunosuppression is most often due to drug therapies which either kill or functionally inactivate lymphocytes. Various chemotherapeutic drugs are administered to cancer patients, and these drugs are usually cytotoxic to both mature and developing lymphocytes as well as to granulocyte and monocyte precursors. Thus, cancer chemotherapy is almost always accompanied by a period of immunosuppression and increased risk of infections. Radiation treatment of cancer carries the same risks. Medications (granulocyte-colony stimulating factor) exist for increasing neutrophils in blood to combat infections that occur after cancer chemotherapy, but no medications are currently used for restoring lymphocytic functions. Major surgery, for example repair of aneurysms or by-pass operations, also decrease immune function in humans. The reasons for the decline in blood lymphocytes that occur because of major surgery are not clear, but an agent that elevates lymphocyte functions in such patients have therapeutic value in decreasing the likelihood of infections.

One final form of acquired immunosuppression that should be mentioned results from the absence of a spleen, caused by surgical removal of the organ after trauma or for the treatment of certain hematologic diseases or as a result of infarction in sickle cell disease. Patients without spleens are more susceptible to infections by some organisms, particularly encapsulated bacteria such as Streptococcus pneumoniae. The spleen is apparently required for the induction of protective humoral immune responses to such organisms. Bestim would help individuals without a spleen or without a thymus in resistance against infection by micro-organisms.

Data concerning the inventive peptides, as well as several synthesis methods, will now be illustrated by the following examples, which are intended to illustrate, but not limit, the invention.

EXAMPLE 1

Preparation of Inventive Compounds and Their Pharmaceutical Compositions

Materials and Equipment

Reagents. N-benzyloxycarbonyl-D-glutamic acid α-benzyl ester and N-benzyloxycarbonyl-L-glutamic acid α-benzyl ester were prepared as described in Moore et al., J. Chem. Soc., 2349 (1966), and L-tryptophan benzyl ester p-toluenesulphonate were prepared as described in Arai et al., J. Org. Chem., 48, 121 (1983). D-tryptophan, N-methylmorpholine, isobutyl chloroformate, palladium-charcoal catalyst (10%), N-hydroxysuccinimide, dicyclohexylcarbodiimide, N,N-dimethylformamide, tetrahydrofurane, acetonitrile were purchased from Fluka, and trifluoroacetic acid was purchased from Merck.

Thin-layer Chromatography (TLC). Ascending TLC was performed on precoated plates Kieselgel 60 $F_{254}$ (Merck) using the following solvent systems (by vol.):

A, chloroform/methanol/acetic acid 90:8:2;

B, 2-propanol/25% NH₄OH/water 50:5:15;

C, butanol/acetic acid/water 3:1:1.

Peptides were located with UV light, ninhydrin and $J_2$.

High Performance Liquid Chromatography (HPLC). For all HPLC separations the same solvent system was used: solvent A—0.1% trifluoroacetic acid in water and solvent B—acetonitrile.

Analytical runs were carried out on a Gilson chromatograph consisting of two pumps (Model 302), autosampler (Model 402), spectrophotometer (Model 116), Data Master (Model 621), and analytical column Zorbax ODS 4.6×150 mm, 5 g. Flow rate—1 ml/min. Peptide was controlled at 230 nm. Eluent—linear gradient of 10–40% B or 10–90% over 20 min.

Preparative purification was carried out on a Gilson chromatograph consisting of two pumps (Model 303), dynamometric mixer (Model 811), collector fractions (Model 202), spectrophotometer (Holochrome), and preparative column Zorbax ODS 21.2×250 mm, 8 μ. Flow rate—10 ml/min. Peptide was controlled at 230 nm. Eluent—linear gradient of 0–40% B over 80 min.

Nuclear Magnetic Resonance. All spectra were recorded with a Brucker CPX-300 spectrometer equipped with an Aspect 2000 computer, operating in the Fourier transform mode with quadrature detection at 300 MHz for protons. 50 mg of peptide was dissolved in 0.5 ml of $CD_3OD$ in which the $^1H$ residual signal was taken as reference at 3.35 ppm. Unless otherwise specified, typical acquisition parameters were: temperature—ambient, spectral width—4500 Hz, pulse width—1 μs (6°), and 8192 data points in time domain. Processing was performed with 16384 points addresses. Relax delay—2 s.

EXAMPLE 1A

γ-D-glutamyl-L-tryptophan

N-Benzyloxycarbonyl-γ-D-glutamyl-L-tryptophan Dibenzyl Ester

A solution of N-benzyloxycarbonyl-D-glutamic acid α-benzyl ester (0.74 g, 2 mmol) and N-methylmorpholine (0.22 ml, 2 mmol) in dry tetrahydrofurane is cooled to −15° C. Isobutyl chloroformate (0.28 ml, 2 mmol) is added and the mixture allowed to stand at −10° C. for 3 minutes for the formation of the mixed anhydride. At that time a solution of L-tryptophan benzyl ester p-toluenesulphonate (0.93 g, 2 mmol) and N-methylmorpholine (0.22 ml, 2 mmol) in dry tetrahydrofurane, (15 ml) cooled to −5° C., is added and the reaction mixture is set aside in a refrigerator at about 5° C. Next day the solution is filtered from the salt, washed by dry tetrahydrofurane (20 ml) and evaporated in vacuo. The residue is dissolved in ethylacetate (50 ml), washed with equal volumes water, 2N $H_2SO_4$ solution, water, 5% $NaHCO_3$ solution, and water again. It is dried over anhydrous $Na_2SO_4$, filtered from the drying agent and concentrated in vacuo to about 10 ml. On dilution with hexane (50 ml) the product separates. Yield 820 mg (62%). Rf(A)—0.75.

γ-D-glutamyl-L-tryptophan

A solution of N-benzyloxycarbonyl-γ-D-glutamyl-L-tryptophan dibenzyl ester (0.6 g, 0.9 mmol) in methanol (30 ml) is hydrogenated over Pd/C (10%, 200 mg) during 5 hours. The catalyst is removed by filtration across charcoal and the filtrate is evaporated to dryness. Yield 260 mg.

The obtained peptide is purified by means preparative HPLC and lyophilized. Yield 190 mg. RF(B)—0.5, RF(C)—0.45. As earlier noted, this particularly preferred embodiment is sometimes referred to as "SCV-07."

TABLE 1

| Proton Chemical Shifts (ppm) of γ-D-glutamyl-L-tryptophan | | | | |
|---|---|---|---|---|
| Residue | Hα | Hβ | Hγ | Other |
| Trp | 4.75 | 3.2–3.4 | | H4-7.65; H7-7.35; H2-7.15; H6-7.1; H5-7.05 |
| Glu | 3.65 | 2.4 | 2.1 | |

TABLE 2

| $^{13}C$ Chemical Shifts (ppm) of γ-D-glutamyl-L-tryptophan | | | | |
|---|---|---|---|---|
| Residue | CO | Cα | Cβ | Cγ | Other |
| Trp | 176.19 | 55.17 | 27.65 | | H4-111.08; H8-112.35; H11-119.25; H9-119.81; H10-122.38; H5-124.58; H7-128.76; H6-137.87 |
| Glu | 173.96 174.68 | 55.17 | 28.48 | 32.71 | |

EXAMPLE 1B

γ-L-glutamyl-D-tryptophan

N-Benzyloxycarbonyl-γ-L-glutamyl-D-tryptophan α-Benzyl Ester

A solution of N-benzyloxycarbonyl-L-glutamic acid α-benzyl ester (0.99 g, 2.6 mmol) and N-hydroxysuccinimide (0.3 g, 2.6 mmol) in N,N-dimethylformamide 96 ml) is cooled in an ice-water bath and a solution of dicyclohexylcarbodiimide (0.56 g, 2.7 mmol) in N,N-dimethylformamide (3 ml) is added with stirring. The mixture is stirred 1 hour at 0° C. and overnight at room temperature. The separated N,N-dicyclohexylurea is removed by filtration and D-tryptophan (0.64 g, 3.1 mmol) and triethylamine (0.46 ml, 3.3 mmol) are added to filtrate. The mixture is stirred during 16 hours at room temperature and diluted by water (50 ml). The separated oil is extracted by ethylacetate (3×20 ml) and combined organic layer is washed with $2NH_2SO_4$ solution (2×20 ml) and water (4×30 ml), dried over $Na_2SO_4$, filtered from the drying agent and concentrated in vacuo to about 10 ml. On dilution with hexane (30 ml) the product separates. Yield 1.2 g (81%). Rf(A)—0.7.

γ-L-Glutamyl-D-tryptophan

A solution of N-benzyloxycarbonyl-γ-L-glutamyl-D-tryptophan α-benzyl ester (0.6 g, 0.9 mmol) in methanol (30 ml) is hydrogenated over Pd/C (10%, 200 mg) during 2 hours (TLC control). The catalyst is removed by filtration across charcoal and the filtrate is evaporated to dryness. Yield 285 mg.

The obtained peptide is purified by means preparative HPLC and lyophilized. Yield 180 mg. Rf(B)—0.5, Rf(c)—0.45.

γ-L-glutamyl-D-tryptophan has the same $^1H$ NMR and $^{13}C$ NMR spectra as γ-D-glutamyl-L-tryptophan.

EXAMPLE 1C

Solid Phase Synthesis of β-L-aspartyl-L-tryptophan

The desired molecule was synthesized using 1% divinylbenzene cross-linked polystyrene as solid support. 0.1 g of Na-tert-Boc-Ninformyl-L tryptophan-Merrifield resin (content of Trp 0.7 mmol/g resin) is placed into reaction vessel. The program of automated synthesis is as follows.

TABLE 3

Schedule for Automated Peptide Synthesis

| Step | Reagent | No. Repeats | Vol (ml) | Time (min) |
|---|---|---|---|---|
| 1 | 50% TFA in $CH_2Cl_2$ | 2 | 5 | 2 + 30 |
| 2 | $CH_2Cl_2$ | 6 | 8 | 2 |
| 3 | 5% DIEA in $CH_2Cl_2$ | 3 | 5 | 2 |
| 4 | $CH_2Cl_2$ | 6 | 8 | 2 |
| 5 | coupling* | 1 | 4 | 120 |
| 6 | DMAA | 2 | 8 | 2 |
| 7 | 2-propanol | 2 | 8 | 2 |
| 8 | $CH_2Cl_2$ | 2 | 8 | 1 |
| 9 | Ninhydrin test** | — | — | — |

TFA-trifluoroacetic acid, DIEA-diisopropylethylamine, DMAA-dimethylacetamide.
*coupling was carried out by active ester of 1-hydroxybenzotriazole (HOBt) which was prepared from three equivalents of Boc-L-Asp-α-OBzl, HOBt and dicyclohexylcarbodiimide (DCI) in DMAA for 30 minutes on ice.
**completion of coupling was verified by the Kaiser ninhydrin test (Kaiser et al., Anal. Biochem., 34:595, 1970). Incomplete coupling was repeated once more time.

Peptide was deprotected and cleaved from polymer with liquid hydrogen fluoride (HF) containing 10% anisole and 10% m-cresol at 0° C. for 60 minutes. HF was removed in vacuo at 0° C., peptide was extracted with 30% aqueous acetic acid, washed with ethyl ether, lyophilized and after deformylation with 0.2N sodium hydroxide was purified by preparative high-performance liquid chromatography (HPLC).

All Bestim analogs may be synthesized according to the same scheme as in the Table 3 schedule above, with the use of different Boc-derivatives at stage 5 being the only difference.

Verification of Synthesis

For example, Bestim was characterized by:
1. High-Performance Liquid Chromatography (HPLC), using a Chromatograph Gilson (France), eluent 0.1% TFA/acetonitrile, gradient 10–40%, 14 min run, column Delta-Pack C-18, 300 Å, 5 μm, 3.9×150 mm. The retention time of the product was 8.1 min and its purity, measured as the integrated area under the HPLC peak was 99.7%.
2. Amino acid analysis: using a LKB Amino acid analyzer Alpha Plus 4151 the product was hydrolyzed in 4N methansulfonic acid, containing 0.2% of tryptamine in vacuo, at 115° C., 24 hours. The peptide content of glutamic acid 1.0, tryptophan 0.94, confirming the presence of the desired residues.
3. Thin-layer chromatography (TLC): system I—n-butanol:ethylacetate:acetic acid:water=1:1:1:1, Rf=0.72; system 2—sec-butanol:acetic acid:toluene:water=6:1:2:1, Rf=0.4.
4. Nuclear magnetic resonance spectrometry (NMR): NMR spectrometer Bruker GXP-300 equipped with Aspect 200 computer. In carbon NMR spectrum of the peptide (0.001 M/1 solution) were detected: for Glu—at 30.0; 31.0; 57.2; 176.6; 178.3 ppm; for Trp—at 35.7; 58.3; 113.1; 116.6; 123.4; 124.3; 126.6; 129.0; 131.0; 140.3; 179.4 ppm.
5. Fast atom bombardment mass spectrometry (FAB-MS), molecular ion: calculated, 334.13 Da; found 333.73.

Preparation of the inventive compounds in a pharmaceutically acceptable salt form is illustrated by Example 1D below, followed by formulation of tablets as described in Example 1E.

EXAMPLE 1D

Preparation of H-γ-D-Glu-L-Trp Sodium Salt

N-benzyloxycarbonyl-γ-D-Glu-L-Trp-α-benzy 1 ester (5 g, 0.087 M) was dissolved in methanol (40 ml) and $NaHCO_3$ (0.73 g, 0.087 M) was added. The air was displaced by slow stream of nitrogen and 10% palladium-on-charcoal catalyst (2.5 g in 30 ml of water) was added. Once again a slow stream of nitrogen was led through the flask, then the introduction of slow stream of hydrogen was started. The catalyst was kept in suspension by vigorous stirring. In 4 hours catalyst was removed by filtration and washed by methanol (10 ml). The filtrate was evaporated in vacuo and the residue triturated with acetonitrile. The solid product was collected on a filter, washed with acetonitrile and dried in vacuo.

Yield: 2.14 g (70%).

EXAMPLE 1E

Formulation of Tablets

The Example 1A inventive peptide (γ-D-glutamyl-L-tryptophan) was formulated into tablets with either 98.9% glycine, 1% magnesium stearate, and 0.1% inventive peptide, or 94.9% glycine, 5% starch, and 0.1% inventive peptide. Each 100 mg tablet contained 100 μg of the inventive analog.

EXAMPLE 2

Bestim and Bestim Analog Studies In Vivo
Influence on Interleukin 2 (IL-2) Production Species: Mouse (CBA strain).

Assay: Peptides γ-L-Glu-L-Trp (Bestim) and γ-D-Glu-L-Trp (Bestim analog) were administered into mice per os in a form of water solution at different doses indicated in the table once per day by 5 consecutive days. Five animals were used for each peptide dose. 48 hours later spleens were removed and spleen cells were cultured for additional 24 hours in vitro in the presence of IL-2 production inducer ConA (5 μg/ml) in RPMI-1640 medium supplemented with 10% fetal calf serum in 96-well flat-bottom culture plates. IL-2 levels in the supernatants were measured in the bioassay using murine IL-2-dependent cell line CTLL-2 (Gillis et al., 1978).

TABLE 4

Effect of Bestim and its Analogs on IL-2 Production by Murine Spleen Cells

| Peptide dose (μg/kg) | γ-D-Glu-L-Trp (SCV-07) | γ-L-Glu-L-Trp (Bestim) |
|---|---|---|
| 10.0 | 132.2 ± 9.3* | 56.7 ± 4.5 |
| 0.1 | 129.2 ± 9.8* | 47.2 ± 8.9 |
| 0.001 | 103.4 ± 7.5* | 115.9 ± 8.6* |
| 0.00001 | 85.9 ± 5.0* | 65.2 ± 6.2 |
| Control | 68.3 ± 4.9 | 68.3 ± 4.9 |

*significant difference with the control, $p < 0.05$

Conclusion: Peptide γ-D-Glu-L-Trp (Inventive Bestim analog) had a higher biological activity compared to that of Bestim. IL-2 induction was observed in a more wide dose range, and at high doses this analog did not give decrease in IL-2 induction.

EXAMPLE 3

Influence on Thy-1 Antigen Expression by Murine Bone Marrow T-Cell Precursors

Protocol: Bone marrow cells were obtained from CBA mice femur bones and incubated with peptides in vitro in microtitration (Terasaki) plates in Eagle's medium for one hour at 37° C. Thy-1 antigen expression was determined by complement-dependent cytotoxicity assay using anti Thy-1 antibodies.

TABLE 5A

Changes in the Numbers of Thy-1 Antigen Expressing Cells in Murine Bone Marrow Cultured in the Presence of Inventive Peptides Analogs

| Peptide Concentration (μg/kg) | Thy-1 Antigen Expressing Cells (%) | | |
|---|---|---|---|
| | γ-L-Glu-D-Trp | γ-D-Glu-L-Trp (SCV-07) | γ-L-Glu-L-Trp (Bestim) |
| 10.0 | 39.4 ± 2.2 | 63.6 ± 4.2 | 35.0 ± 3.0 |
| 1.0 | 44.3 ± 5.4 | 47.3 ± 1.6 | 39.6 ± 4.6 |
| 0.1 | 42.2 ± 4.4 | 38.4 ± 4.4 | 38.5 ± 2.8 |
| 0.01 | 35.6 ± 4.1 | 36.3 ± 4.9 | 38.0 ± 3.1 |
| 0.001 | 40.0 ± 1.6 | 37.6 ± 1.2 | 32.2 ± 2.8 |
| 0.0001 | 33.7 ± 2.8 | 37.2 ± 2.6 | 30.0 ± 2.4 |
| 0.00001 | 29.4 ± 1.7 | 36.2 ± 3.2 | 24.0 ± 2.0 |
| Control | | 14.7 ± 2.4 | |

Significant difference with the control, $p<0.05$, was observed.

Conclusion: The inventive peptide γ-D-Glu-L-Trp had the highest activity compared to activity of Bestim and another inventive analog, γ-L-Glu-D-Trp.

TABLE 5B

Changes In the Numbers Of Thy-1 Antigen Expressing Cells in Murine Bone Marrow Cultured in the Presence of Inventive Peptides

| Peptide Concentration (μg/ml) | Numbers of Thy-1 antigen expressing cells (%) | | |
|---|---|---|---|
| | Peptide 1** | Peptide 2 | Peptide 3 |
| 10.0 | 55.4 ± 2.4* | 44.8 ± 4.0* | 41.9 ± 3.2* |
| 1.0 | 51.4 ± 2.6* | 42.5 ± 3.6* | 38.0 ± 2.9* |
| 0.1 | 49.4 ± 2.3* | 22.5 ± 2.8 | 33.9 ± 2.1* |
| 0.01 | 35.7 ± 2.1* | 18.2 ± 2.3 | 27.3 ± 2.1* |
| 0.001 | 14.9 ± 1.7 | 16.4 ± 1.9 | 13.0 ± 1.3 |
| 0.0001 | 12.7 ± 1.9 | 17.9 ± 2.1 | 12.9 ± 1.4 |
| 0.00001 | 12.3 ± 1.6 | 15.6 ± 2.0 | 13.4 ± 1.7 |
| Control | | 13.9 ± 1.9 | |

| Peptide Concentration (μg/ml) | Numbers of Thy-1 antigen expressing cells (%) | |
|---|---|---|
| | Peptide 4** | Peptide 5 |
| 10.0 | 41.2 ± 4.0* | 66.3 ± 4.5* |
| 1.0 | 39.2 ± 4.1* | 64.3 ± 4.4* |
| 0.1 | 37.1 ± 3.6* | 57.0 ± 4.0* |
| 0.01 | 36.3 ± 2.9* | 54.0 ± 3.9* |
| 0.001 | 25.6 ± 2.8 | 40.0 ± 4.1* |
| 0.0001 | 24.2 ± 2.9 | 29.0 ± 2.8* |
| 0.00001 | 23.0 ± 2.7 | 14.0 ± 1.8 |
| Control | | 14.8 ± 2.1 |

*significant difference with the control, δ < 0.05.
**the peptides used were:
1. beta-L-aspartyl-L-tryptophan
2. acetyl-gamma-D-glutamyl-L-tryptophan
3. beta-D-aspartyl-L-tryptophan
4. gamma-D-glutamyl-L-tryptophan-amide
5. gamma-D-glutamyl-L-tryptophan (SCV-07)

EXAMPLE 4

In Vitro Bestim Analogs' Biological Activity

Peptides: Bestim and several inventive analogs were prepared in lyophilized form. Just before the experiment all peptides were solubilized in water to prepare solutions with different substance concentrations.

Influence on IL-2 Production in Culture

Protocol. Spleens from CBA mice were removed, splenocytes isolated and cultured in RPMI-1640 medium supplemented with 10% fetal calf serum in 96-well flat-bottom culture plates. IL-2 production was induced with 5 μg/ml Con A in 24 hour culture. Peptides at desired concentrations were added to cell cultures at "0" time. IL-2 levels in culture supernatants were determined using IL-2 dependent CTLL-2 cell line (Gillis et al., 1978).

TABLE 6

Changes in Con-A Induced IL-2 Production by Murine Spleen Cells in Culture in the Presence of Bestim Analogs

| Peptide Concentration (μg/kg) | IL-2 Level in the Supernatants (IU/ml) | | |
|---|---|---|---|
| | γ-L-Glu-D-Trp | γ-D-Glu-L-Trp (SCV-07) | γ-L-Glu-L-Trp (Bestim) |
| 10.0 | 62.8 ± 3.2* | 65.5 ± 3.7* | 59.9 ± 3.0* |
| 1.0 | 57.4 ± 4.8 | 80.9 ± 6.7* | 61.4 ± 3.3* |
| 0.1 | 57.9 ± 3.2 | 87.2 ± 7.1* | 57.3 ± 4.0 |
| 0.01 | 59.9 ± 4.5 | 73.8 ± 6.3* | 56.6 ± 3.7 |
| 0.001 | 60.4 ± 5.9 | 65.9 ± 4.0* | 54.7 ± 3.2 |
| 0.0001 | 52.6 ± 5.0 | 47.9 ± 3.4 | 53.2 ± 3.3 |
| Control | 50.1 ± 3.7 | 50.1 ± 3.7 | 50.1 ± 3.7 |

*significant difference with the control, $p < 0.05$.

EXAMPLE 5

Changes in the Immune System of Patients after Peroral Application

Either of the two tablet formulations described in Example 1E were given to two patients with cancer one month after surgical operation.

First Case Study

Patient: "Eg"

Diagnosis: Colon cancer

Previous therapy: Surgery

SCV-07 therapy: 5 daily peroral tablet application (0.1 mg per day).

TABLE 7

Data on the Changes of Immune Parameters in Patient "Eg" Receiving SCV-07 Tablet Peroral Therapy

| Immune parameters | Before treatment | 2 weeks after the end of 5 days treatment |
|---|---|---|
| Blood lymphocyte counts (%): | | |
| CD3 | 51.2 ± 1.1 | 55.4 ± 1.3 |
| CD4 | 26.2 ± 1.0 | 29.7 ± 1.5 |
| CD8 | 23.1 ± 1.3 | 24.1 ± 1.6 |
| CD4/CD8 ratio | 1.13 | 1.23 |
| CD20 | 20.8 ± 1.4 | 20.4 ± 1.1 |
| Neutrophil migration index | 2.35 | 2.46 |
| Neutrophil nitroblue tetrazolium reduction (U): | | |
| spontaneous | 675 ± 23 | 1031 ± 49 |
| PMA-induced | 6459 ± 132 | 6950 ± 175 |

Second Case Study

Patient: "Ar"

Diagnosis: Colon cancer

Previous therapy: Surgery

SCV-07 therapy: 5 daily peroral tablet application, (0.1 mg per day)

TABLE 8

Data on the Changes of Immune Parameters in Patient "Ar" Receiving SCV-07 Tablet Peroral Therapy

| Immune parameters | Before treatment | 2 weeks after the end of 5 days treatment |
|---|---|---|
| Blood lymphocyte counts (%): | | |
| CD3 | 46.3 ± 1.4 | 59.2 ± 1.3 |
| CD4 | 23.4 ± 1.2 | 31.0 ± 1.7 |
| CD8 | 23.5 ± 1.1 | 27.1 ± 1.9 |
| CD4/CD8 ratio | 1.0 | 1.14 |
| CD20 | 11.4 ± 1.0 | 14.3 ± 0.9 |
| Neutrophil migration index | 1.25 | 3.07 |
| Neutrophil nitroblue tetrazolium reduction (U): | | |
| spontaneous | 401 ± 38 | 1646 ± 97 |
| PMA-induced | 5007 ± 245 | 5111 ± 304 |

Influence of the inventive peptide γ-D-glutamyl-L-tryptophan on the human neutrophilic leukocytes functional activity was determined according to the changes in the level of free oxygen radicals production using spontaneous luminol-dependent chemi-luminescence assay (Muto et al., 1986). Samples of the donors' whole blood were inserted into working cuvets of the 1251 Luminometer (LKB) together with peptides diluted in saline in a concentration indicated in the table. Luminol was added to each cuvet and cuvets were incubated for 10 min. After this cuvets were incubated in the luminometer wells for 40 min at 37° C. and constant agitation. The quantity of developed superoxide radicals was calculated using "Lumina" computer program and expressed as light sum for 40 min (mV/min). Each sample was studied in triplicate.

TABLE 9

Influence of Peptide on Luminol Enhanced Neutrophil Chemiluminescence in Human Whole Blood Cell Culture

| Inventive Peptide ($\mu$g/ml) | Chemiluminescence in unstimulated cells | | Chemiluminescence in PMA activated cells | |
|---|---|---|---|---|
| | Peak value (mv) | Light sun-40 min (mv/min) | Peak value (mv) | Light sum-40 min (mv/min) |
| 1.0 | 0.71 ± 0.02 | 25.7 ± 0.13 | 3.40 ± 0.06* | 75.9 ± 1.5* |
| 0.1 | 0.72 ± 0.02 | 27.2 ± 0.93 | 2.57 ± 0.40 | 60.3 ± 0.8 |
| 0.01 | 0.73 ± 0.04 | 27.9 ± 0.85 | 3.03 ± 0.99 | 63.0 ± 0.7 |
| Control | 0.66 ± 0.07 | 25.2 ± 0.09 | 2.90 ± 0.12 | 64.9 ± 4.0 |

*significant difference with control, $P < 0.05$

Studies of the Influence of Inventive Peptides on Human Leukocyte Chemotaxis

The chemotactic assay was carried out using agarose migration technique described by Nelson et al. (1972). Agarose was dissolved in 199 culture medium supplemented with 10% fetal calf serum to a final concentration 1%. This mixture was transferred to a tissue culture dish and allowed to gel. Series of wells 2 mm in diameter and spaced 3 mm apart were cut in the gel. 10 $\mu$l of neutrophils (2.5×10⁶ cells per ml) were added to the central well. Other wells were filled on one side with medium to measure random migration, while those on the other side were filled with the chemotactic factor FMLP at $10^{-7}$ M, to measure stimulated migration. Dishes were incubated in a $CO_2$ incubator for 120 min. Peptides at desired concentrations were added to the cells at "0" time. Cell migration was read under microscope with a microscale and expressed as chemotactic index: stimulated migration/random migration.

TABLE 10

| | Peptide concentration, $\mu$g/ml | | |
|---|---|---|---|
| Peptides** | 100 | 10 | 1 |
| 1 | 1.47 ± 0.04 | 1.75 ± 0.25 | 1.71 ± 0.20 |
| 2 | 1.73 ± 0.07 | 1.79 ± 0.01 | 2.33 ± 0.17* |
| 3 | 2.17 ± 0.17* | 1.78 ± 0.20 | 1.73 ± 0.10 |
| 4 | 2.13 ± 0.34 | 1.71 ± 0.15 | 1.75 ± 0.13 |
| 5 | 2.50 ± 0.30* | 1.77 ± 0.17 | 1.81 ± 0.11 |
| 6 | 2.19 ± 0.30 | 1.93 ± 0.29 | 1.61 ± 0.15 |
| Control | | 1.77 ± 0.05 | |

*significant difference with the control, $\delta < 0.05$.
**the peptides used were:
1. beta-L-aspartyl-L-tryptophan
2. acetyl-gamma-D-glutamyl-L-tryptophan
3. beta-D-aspartyl-L-tryptophan
4. gamma-D-glutamyl-L-tryptophan-amide
5. gamma-D-glutamyl-L-tryptophan (SCV-07)
6. gamma-D-glutamyl-L-tryptamine Studies of the Influence of Inventive Peptides on Human Leukocyte Phagocytosis Human neutrophilic leukocytes obtained from donor's blood by Ficoll-Pack separation were transferred to silicone-treated tubes at a concentration 2×10⁶ cells per ml in Eagle's culture medium supplemented with 10% fetal calf serum. Yeast cells opsonized with huan sera were used as an object of phagocytosis. Yeast cells were added into tubes (10 yeast cells per 1 neutrophil) and cell suspension was incubated in a $CO_2$ incubator for 40 min. After this cells were washed by centrifugation, cell smears on glass slides were prepared and stained by Giemsa stain. Phagocytic cells were calculated under microscope.

TABLE 11

| | Peptide concentration, $\mu$g/ml | | |
|---|---|---|---|
| Peptides** | 100 | 10 | 1 |
| 1 | 33.3 ± 1.2* | 36.0 ± 7.5* | 32.3 ± 1.8* |
| 2 | 34.3 ± 1.2* | 29.5 ± 0.5* | 30.0 ± 1.1* |
| 3 | 22.3 ± 1.9 | 21.0 ± 5.0 | 23.0 ± 5.6 |
| 4 | 20.7 ± 5.2 | 18.0 ± 2.7 | 16.7 ± 2.7 |
| 5 | 25.0 ± 1.4* | 25.7 ± 2.7* | 17.0 ± 1.0 |
| 6 | 19.0 ± 2.3 | 22.0 ± 4.0 | 22.0 ± 3.0 |
| Control | | 16.7 ± 1.5 | |

*significant difference with the control, $P < 0.05$.
**the peptides used were:
1. beta-L-aspartyl-L-tryptophan
2. acetyl-gamma-D-glutamyl-L-tryptophan
3. beta-D-aspartyl-L-tryptophan
4. gamma-D-glutamyl-L-tryptophan-amide
5. gamma-D-glutamyl-L-tryptophan (SCV-07)
6. gamma-D-glutamyl-L-tryptamine Influence of Inventive Peptides on the Rat Thymocytes Proliferation In Vitro Triplicate cultures of inbred white rat thymocytes at 5×10⁶ per ml were cultured with peptides for 72 hours in $CO_2$ incubator in flat-bottom 96-well culture plates in RPMI-1640 medium supplemented with 1% heatinactivated fetal bovine serum, 2 mM L-glutamine, 80 μg/ml gentamycin, 5 μg/ml Polymixin B and 0.5 μg/ml Concanavalin A. Sixteen hours before the end of the culture period cells were pulse labelled with $^3$H-thymidine. Cells were harvested on glass fiber filters with Titertek cell harvester and counted in beta liquid scintillation counter. Proliferation rate was expressed as counts per min.

TABLE 12

| Peptide Concentration | Proliferation rate (counts per min) | | |
|---|---|---|---|
| (μg/ml) | Peptide 1 | Peptide 2 | Peptide 3 |
| 1.0 | 58720 ± 2340* | 52300 ± 2490 | 49700 ± 790 |
| 0.1 | 53110 ± 485 | 53340 ± 1590 | 50190 ± 1780 |
| 0.01 | 46590 ± 1190 | 51950 ± 5910 | 56510 ± 3970 |
| 0.001 | 55010 ± 5350 | 56790 ± 1880* | 55530 ± 2750 |
| 0.0001 | 51230 ± 2030 | 52080 ± 1880 | 51430 ± 2050 |
| Control | | 49000 ± 1420 | |

| Peptide Concentration | Proliferation rate (counts per min) | |
|---|---|---|
| (μg/ml) | Peptide 4 | Peptide 5 |
| 1.0 | 53330 ± 1370 | 49420 ± 1210 |
| 0.1 | 48690 ± 1790 | 53180 ± 1910 |
| 0.01 | 48100 ± 1950 | 59480 ± 2250* |
| 0.001 | 50740 ± 2190 | 61340 ± 2340* |
| 0.0001 | 50960 ± 1050 | 57880 ± 1560* |
| Control | | 49000 ± 1420 |

*significant difference with the control, P < 0.05.
**the peptides used were:
1. beta-L-aspartyl-L-tryptophan
2. acetyl-gamma-D-glutamyl-L-tryptophan
3. beta-D-aspartyl-L-tryptophan
4. gamma-D-glutamyl-L-tryptophan-amide
5. gamma-D-glutamyl-L-tryptophan (SCV-07)

In conclusion, the inventive peptides have immunostimulatory properties and can stimulate IL-2 production by splenic lymphocytes, induce precursor T-lymphocyte maturation, and stimulate T-cell proliferation. In particular, the preferred inventive peptide γ-D-Glu-L-Trp (SCV-07) is shown to increase immune function through stimulation of human neutrophilic leukocyte functional activity, especially phagocytosis and oxygen radical production. The inventive peptides, particularly SCV-07, are shown to increase total T-lymphocyte and T-helper lymphocyte numbers and CD4/CD8 ratio in peripheral blood. Finally, the inventive peptides, particularly SCV-07 have also been shown to stimulate human neutrophilic leukocyte migration and bactericidal activity.

It is to be understood that while the invention has been described above in conjunction with preferred specific embodiments, the description and examples are intended to illustrate and not limit the scope of the invention, which is defined by the scope of the appended claims.

It is claimed:

1. A compound with at least two amino acid residues and having the structure of Formula 1:

FORMULA 1

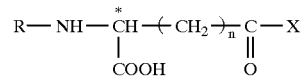

where n is 1 or 2, R is hydrogen, an acyl having 2 to 10 carbon atoms, or an alkyl having from 1 to 6 carbons, and X is L-tryptophan or D-tryptophan, and wherein the α carbon marked with an asterisk in Formula 1 has a stereoconfiguration, when n is 2, that is different from the stereoconfiguration of X.

2. The compound as in claim 1 wherein X is L-tryptophan.

3. The compound as in claim 1 wherein X is D-tryptophan.

4. The compound as in claim 1 in a pharmaceutically acceptable salt form.

5. The compound γ-D-glutamyl-L-tryptophan.

6. The compound β-L-aspartyl-L-tryptophan.

7. The compound β-D-aspartyl-L-tryptophan.

8. A pharmaceutical composition comprising the compound of either claim 5, 6, or 7 in admixture with a pharmaceutically acceptable carrier.

9. A therapeutic method comprising:
   administering to a patient a therapeutic dose, the dose having a compound as in claim 3 in the range of about 1 ng to about 1000 μg per kg of body weight.

10. The method as in claim 9 wherein the administration is as a single dose or a plurality of doses given intermittently.

11. The method as in claim 10 wherein the administration is by parenteral injection, oral or nasal inhalation, or oral ingestion.

12. An immunomodulatory therapeutic method comprising:
    administering to a patient a dose in the range of about 1 ng to about 1000 μg of body weight a compound in a pharmaceutically acceptable form and having the structure of Formula 1:

FORMULA 1

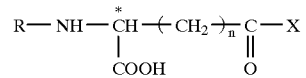

where n is 1 or 2, R is hydrogen, an acyl having 2 to 10 carbon atoms, or an alkyl having from 1 to 6 carbons, and X is L-tryptophan or D-tryptophan, and wherein the a carbon marked with an asterisk in Formula 1 has a stereoconfiguration, when n is 2, that is different from the stereoconfiguration of X.

13. The method as in claim 12 wherein the administering is effective to modulate a patient's immune system.

14. The method as in claim 12 wherein the compound administered includes γ-D-glutamyl-L-tryptophan.

* * * * *